United States Patent
Reimers et al.

(10) Patent No.: US 6,864,331 B1
(45) Date of Patent: Mar. 8, 2005

(54) PROCESS FOR THE PRODUCTION OF POLYMERS

(75) Inventors: Jay Reimers, Houston, TX (US); Thanh Nguyen, Sugar Land, TX (US)

(73) Assignee: Fina Technology, Inc., Houston, TX (US)

(*) Notice: Subject to any disclaimer, the term of this patent is extended or adjusted under 35 U.S.C. 154(b) by 0 days.

(21) Appl. No.: 10/731,729

(22) Filed: Dec. 9, 2003

(51) Int. Cl.$^7$ .................................................. C08F 2/00
(52) U.S. Cl. ..................... 526/59; 526/346; 526/352; 526/348; 356/319; 356/326
(58) Field of Search .................. 526/59, 346, 348, 526/352; 356/319, 326

(56) References Cited

U.S. PATENT DOCUMENTS

| | | | |
|---|---|---|---|
| 4,370,201 A | 1/1983 | Lowenhaupt | 201/1 |
| 4,743,339 A | 5/1988 | Faix et al. | 162/49 |
| 5,151,474 A | * 9/1992 | Lange et al. | 526/60 |

* cited by examiner

Primary Examiner—William K. Cheung
(74) Attorney, Agent, or Firm—Madan, Mossman & Sriram

(57) ABSTRACT

Disclosed is a process for preparing a polymer. The process includes at least one process stream and the process stream has at least one characteristic of interest. The process further includes passing the process stream past a sensor probe connected to a near-IR spectrophotometer and passing light from a light source through the probe and into the spectrometer wherein the light source, spectrometer and sensor probe are connected by a fiber optic cable. The effect of the interaction of the process stream and the light passing through the senor probe is measured and used to define a value for the characteristic of interest. The value for the characteristic of interest is a component of an algorithm and the algorithm is used, in real time, to monitor, control, or monitor and control the process for preparing a polymer.

22 Claims, 3 Drawing Sheets

PROCESS FOR THE PRODUCTION OF POLYMERS

BACKGROUND OF THE INVENTION

1. Field of the Invention

The present invention relates a process for preparing polymers. The present invention particularly relates to a process for preparing polymers employing on-line analyzers.

2. Background of the Art

Laboratory analysis of production samples during the production of chemical products, and especially when those products are polymers, is a necessary part of the production process. The purposes for these analyses include process control and to ensure product quality, especially during transitions between product grades.

Such chemical analyses can be off-line or on-line. An off-line analysis is accomplished by taking a sample of a process stream and then subjecting it to a laboratory analysis. An on-line analysis is usually accomplished by conducting a portion of the process stream directly to a chemical process analyzer such as an on-line gas chromatograph or by using a probe or other device that can be inserted directly into the process stream. For example, a pH or corrosion probe could be inserted directly into a process stream. On-line chemical process analyzers can offer significant advantages in reducing sample analysis time, which can in turn improve product quality and reduce costs by means of reducing waste in the form of off specification product or prevent premature maintenance which has both direct and indirect costs to chemical manufacturers.

The use of on-line analyzers is known. For example, U.S. Pat. No. 4,370,201 to Lowenhaupt discloses an on-line FTIR process for maintaining coal proportions in a coal blend. U.S. Pat. No. 4,743,339 to Faix, et al., discloses an off-line FTIR process for controlling the digestion of wood pulp. U.S. Pat. No. 5,151,474 to Lange, et al., discloses the use of an FTIR in the production of polyolefins.

SUMMARY OF THE INVENTION

In one aspect, the present invention is a process for preparing a polymer. The process includes at least one process stream and the process stream has at least one characteristic of interest. The process further includes passing the process stream past a sensor probe connected to a near-IR spectrophotometer and passing light from a light source through the probe and into the spectrometer wherein the light source, spectrometer and sensor probe are connected by a fiber optic cable. The effect of the interaction of the process stream and the light passing through the senor probe is measured and used to define a value for the characteristic of interest. The value for the characteristic of interest is a component of an algorithm and the algorithm is used, in real time, to monitor, control, or monitor and control the process for preparing a polymer.

In another aspect, the present invention is a process for preparing a polystyrene. The process includes having at least one process stream and the process stream has at least one characteristic of interest. The process also includes passing the process stream past a sensor probe connected to a near-IR spectrophotometer and passing light from a light source through the probe and into the spectrometer. The light source, spectrometer and sensor probe are connected by a fiber optic cable. The effect of the interaction of the process stream and the light passing through the senor probe is measured and used to define a value for the characteristic of interest and the value for the characteristic of interest is used as a component of an algorithm used in real time to monitor, control, or monitor and control the process for preparing polystyrene.

In still another aspect, the present invention is a process for preparing a polyethylene. The process includes having at least one process stream and the process stream has at least one characteristic of interest. The process also includes passing the process stream past a sensor probe connected to a near-IR spectrophotometer and passing light from a light source through the probe and into the spectrometer. The light source, spectrometer and sensor probe are connected by a fiber optic cable. The effect of the interaction of the process stream and the light passing through the senor probe is measured and used to define a value for the characteristic of interest and the value for the characteristic of interest is used as a component of an algorithm used in real time to monitor, control, or monitor and control the process for preparing polyethylene.

BRIEF DESCRIPTION OF THE DRAWINGS

For a detailed understanding and better appreciation of the present invention, reference should be made to the following detailed description of the invention and the preferred embodiments, taken in conjunction with the accompanying drawings, wherein.

DETAILED DESCRIPTION OF INVENTION

Figure 1:
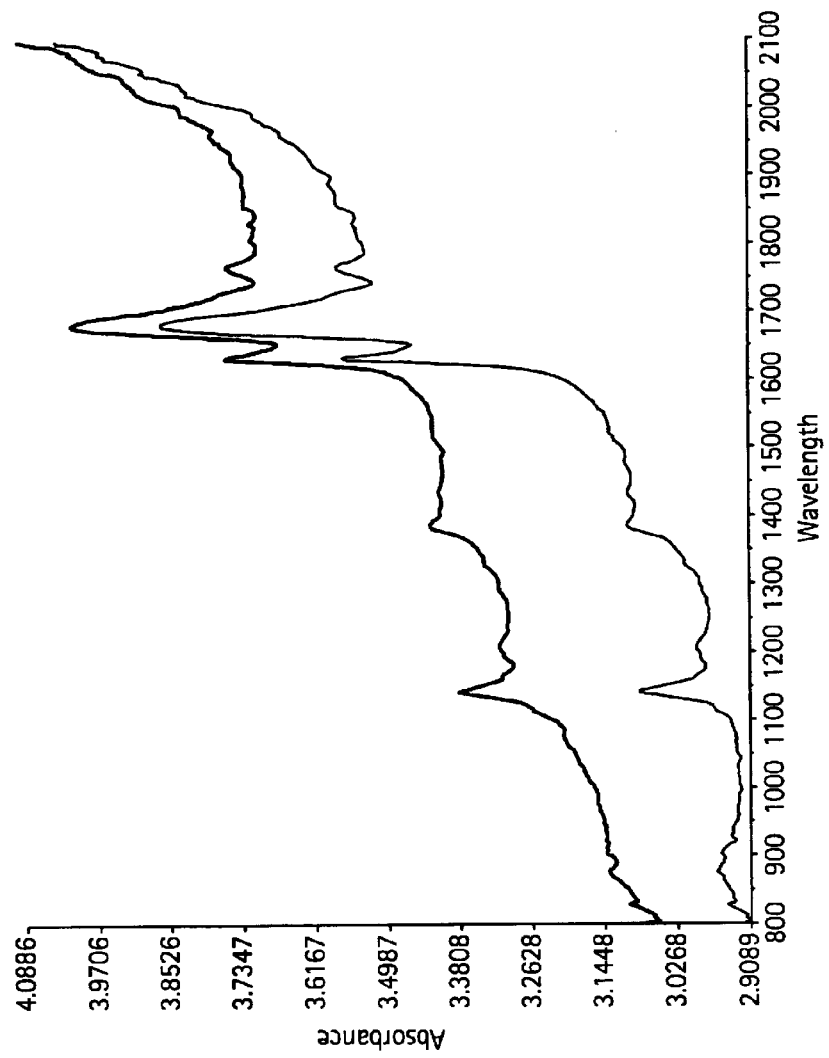
FIG. 1 is a graph showing the near-IR spectra of two impact modified polystyrenes having different particle rubber particle size.

In one embodiment, the present invention is a process for preparing a polymer. The polymer can be any that have a process stream with a characteristic of interest that can be analyzed using an online near infrared (near-IR) analyzer. For the purposes of the present invention, a near-IR analyzer is a spectrophotometer, light source, and probe that can operate over the near-IR range. The near-IR is sometimes also referred to as short wavelength IR and has a peak wavelength from 0.75 to 2.5 microns (u) (750 to 2500 nanometers). Also for the purposes of the present invention, the term process stream means any movement of material within the process that can be passed by a an online near infrared (near-IR) analyzer. For example, a flow through a pipe is a process stream, but so also is the flow through a heat exchanger or reactor.

The polymers that can be prepared using the process of the present invention are any that have a process stream having a characteristic of interest that can be analyzed using near-IR and the resulting function as a component in an algorithm to monitor, control, or monitor and control the production of the polymer. While the process of the present invention can be used to produce any polymer meeting this definition, in one embodiment, the process of the present invention can be used to prepare polystyrene. In another embodiment, the process of the present invention can be used to prepare polyethylene.

In the process of the present invention, a near-IR spectrophotometer is used to monitor, control, or monitor and control the production of a polymer by passing a process stream past a sensor probe connected to a near-IR spectrophotometer. The sensor probes useful with the process of the present invention include any that would be useful for monitoring a characteristic of interest in the process stream. For example, the probe can be selected from the group consisting of transmittance probes, reflectance probes, attenuated reflectance probes, and the like. In one embodiment, the probe used with the process of the present invention is a reflectance probe. In another embodiment, the probe is a double bounce reflectance probe.

In the process of the present invention, a near-IR spectrophotometer is connected to a probe using a fiber optic cable. The probe is optically connected to a light source and a near-IR spectrophotometer. In one embodiment, the near-IR spectrophotometer is local and in another embodiment, the near-IR spectrophotometer is a remote near-IR spectrophotometer. The fiber optic cable may actually be a pair of fiber optic cables wherein a first cable is used to supply light to the subject probe and the second cable is used to bring the light passing through the probe to the spectrophotometer. In one embodiment of the present invention, the optical cables are a bundle of multimode fibers allowing the transmission of light in both directions on a single cable.

The process of the present invention is practiced using a light source capable of producing light in the near-IR spectrum. Any light source capable of producing such light can be used with the present invention. Acousto-Optic Tunable Filters can be used with the present invention to allow the source to be tuned repeatedly to precise wavelengths reliably over long periods of time. Conventionally tuned sources can also be used so long as they have the capability of working in conjunction with the spectrophotometer to make fast, accurate measurements within the near-IR region. The source can be stand alone or it can be a part of an integrated combination of spectrophotometer and source. The near-IR spectrophotometers useful with present invention can be automated and have computers integrated therewith to perform some or all of the processes of interpreting spectra and making calculation therewith.

The process of the present invention can also be used with more than one probe in the same or different process streams having at least one characteristic of interest. One advantage of using a remote spectrophotometer is that it makes it possible to have multiple probes from different parts of a polymer production facility, but only one spectrophotometer to maintain. Another advantage of having a remote spectrophotometer is that it allows such maintenance to be performed in a remote and possibly less hostile environment. In one embodiment of the present invention, there are two probes in the same process stream connected to the spectrophotometer. In another embodiment, there are two probes used with the process of the present invention, but the probes are in different process streams. Use of fiber optic cables allows for the separation of probes and the spectrophotometer optics to range up to 150 meters.

For the purposes of the present invention, a process stream is any part of a polymer production process wherein a liquid or flowable solids stream is passing through a conduit. For example, the process stream can be in a pipe, a reactor, or be an overhead stream from a distillation column. In the practice of the present invention, a probe is interfaced with the process stream. As the materials that make up the process stream move past, some component of the materials interact with the probe to adsorb or refract light within the probe such that the light entering the probe is different in intensity in at least in some part of the near-IR spectrum than light leaving the probe via the fiber optic cable. In the process of the present invention, this difference is then used to determine a value for a characteristic of interest. The measurement can be directly related to the characteristic of interest or indirectly related to the characteristic of interest. For example, one characteristic of interest can be the presence of a compound that is not of itself measurable using near-IR, but which is present in a known relationship with another material that is so measurable. This would be an example of an indirect measurement and is within the scope of the process of the present invention.

In the practice of the process of the present invention, the effect of the interaction of the process stream and the light passing through the senor probe is measured and used to define a value for the at least one characteristic of interest. This determination can be done manually, but in one embodiment of the present invention, this is done using a computer interfaced to the spectrophotometer. Instruments that can be used with the present invention include those manufactured by Analytical Spectral Devices, Inc.; Varian, Inc.; Foss-NIR Systems, and the like. Any near-IR spectrophotometer that can make measurements with sufficient precision and reliability to be useful in monitoring, controlling, or monitoring and controlling a polymer production process can be used with practice of the process of the present invention.

In one embodiment, the present invention is a process for producing polymers such as high density polyethylene produced in an industrial high density polyethylene slurry loop reactor. The process of the present invention includes using the value of the characteristic of interest to control or monitor a production unit. This value can be included in an algorithm that is in a manual calculation process or, in another embodiment, in a manual spreadsheet, or in still another embodiment, it can also be incorporated into the logic circuits of a controller. In one embodiment, the controller is a neural net or other artificial intelligence (AI) controller.

Many operations in a polymer chemical process are routinely controlled using a Proportional Integral Derivative (PID) controller. The algorithm including the value for the characteristic of interest can be incorporated or programmed into such controllers. In an embodiment of the present invention, many PID controllers, are used in conjunction with a second controller that can receive data from the PID controller and then reprogram the PID controller based upon the algorithm including the value of the present invention. An AI controller capable of accepting multiple inputs and sending multiple outputs can also be used with process of the present invention. For example, one such controller is a controller using Process Perfecter® software developed by Pavilion Technologies.

The use of automated controllers with the process of the present invention can be desirable for controlling the polymer production process in real time, but the use of the present invention manually should not be discounted. When incorporated into a spreadsheet, the process of the present invention can be very useful, particularly when changing polymer grades or production rates. In either case, the process of the present invention can be used, for example, to optimize and control a loop reactor to produce polyethylene with desirable properties.

Examples of characteristics of interest for a polyethylene process can include polyethylene solids content, density, and particle size. Any parameter that can be measured in a process stream using a near-IR and that can be useful as a component of a control or monitoring algorithm can be a characteristic of interest in the process of the present invention.

In another embodiment, the process of the present invention is used to prepare polystyrene. In still another embodiment of the present invention, the process is used to prepare impact modified polystyrene. In impact modified polystyrene, a characteristic of interest include but are not limited to styrene content, rubber particle size, polystyrene content, rubber content, and the like.

In the practice of the process of the present invention, the near-IR analyzer can be used at any wavelength or range of wavelengths suitable for determining a value for a characteristic of interest. For example, a process for preparing impact modified polystyrene can use a wavelength range of from about 1100 nm to about 1800 nm.

In the process of the present invention, a value for the at least one characteristic of interest is a component of an algorithm used in real time to monitor, control, or monitor and control the process for preparing a polymer. For the purposes of the present invention, the term "real time" means immediate and without substantial delay. For example, in a conventional process, a test sample in the unit would be collected and then taken to a laboratory. The sample would then be tested and the results then reported to the production unit. The delay due to sample collection, transportation and conventional testing can be minutes but is often hours. Since many polymer units produce polymers at a very fast rate, an hour of production of off specification material could represent tons or even tens of tons of off specification material that may be unusable or, at the very least less valuable.

EXAMPLES

The following examples are provided to illustrate the present invention. The examples are not intended to limit the scope of the present invention and they should not be so interpreted. Amounts are in weight parts or weight percentages unless otherwise indicated.

Example 1

An impact modified polystyrene process is monitored using the process of the present invention. In this process, a process stream includes styrene, polystyrene, diluents, rubber, and mineral oil. A diffuse reflectance probe is installed such that the process stream comes into contact with the probe. The probe is attached to a process near-infrared system from FOSS-NIR Systems using a fiber optic cable. The instrument is fitted with an InGaS detector. Spectra of the process steam are collected at one-minute intervals and a reference scan is taken after every four sample scans. Five products are run during the on-line experiment: 620, 960E, 975E, 825E, and 7240. Based on routine laboratory analysis and the corresponding spectra taken at the same time, regressions are created for percent styrene, polystyrene, diluents, mineral oil, rubber, and the rubber particle size.

When styrene, polystyrene, or diluents are chosen as the constituent for regression, the regression method is always partial least squares, and the number of factors is limited in all cases to a maximum of seven—the total number of constituents plus the effect of temperature. In all cases, the product specific regressions are capable of describing the variations in the spectra with this number of factors or less. For the overall regression, the number of factors is increased to twelve—the number of components plus the total number of products.

Math pretreatments are applied to spectra before the regression. A standard normal variant is applied, and then the second derivative is taken. The standard normal variant describes the scatter in the data, and the second derivative identifies the location and size of a spectral peak. The spectral range for all these components is chosen to be between 1100 nm to 1800 nm, thereby, covering the second overtone region and the part of the first overtone region describing all the C—H vibrations. Outside of this region the spectra are noisy. Each sample is described as unique and leveraged into the regression, as opposed to the random removal of samples during the generation a cross validation. The lab data used to correlate the regressions for percent styrene and percent diluents is obtained directly from routine GC analysis. The diluents are treated collectively.

A correlation between the values for the characteristics of interest a predicted by the process of the present invention and values determined using conventional laboratory practices is made and the results are displayed below in the Table.

FIG. 1 shows the same feed formulation at different rubber particle sizes: the lower spectrum corresponds to 1.7 micron material and the upper spectrum corresponds to an 8.5 micron material. The spectra corresponding to rubber particles size in between these two values naturally falls in between these two spectra. To capture these baseline shifts, it is necessary not to apply any math pretreatment. Any applications would either dampen the baseline shift, in the case of a standard normal variant, or negate it totally, in the case of a second derivative. The samples are leveraged as described previously. While it appears from the spectra that the range of interest should at least capture the large differences in reflectance at small wavelengths, the upper limit could be cut off at 1600 nm.

Hypothetical Example 2

The process of Example 1 is repeated and the values for styrene content are inputted into a neural net artificial intelligence process controller. The value for styrene changes with time to a lower value than the specified value for the product being produced. The neural net controller adjusts several parameters of the process including styrene feed rate and reaction temperature to bring the product back into specification.

Hypothetical Example 3

The process of Example 1 is repeated and the values for polystyrene content are inputted into a neural net artificial intelligence process controller. The value for polystyrene changes with time to a higher value than the specified value for the product being produced. The neural net controller adjusts several parameters of the process including reaction temperature and polymerization initiator concentration to bring the product back into specification.

Example 4

A polyethylene process is monitored using the process of the present invention. A process stream including polyethylene fluff is monitored using the same equipment as is used in Example 1. The constituents for selected for regression are particle size, density and solids percent.

Figure 2:
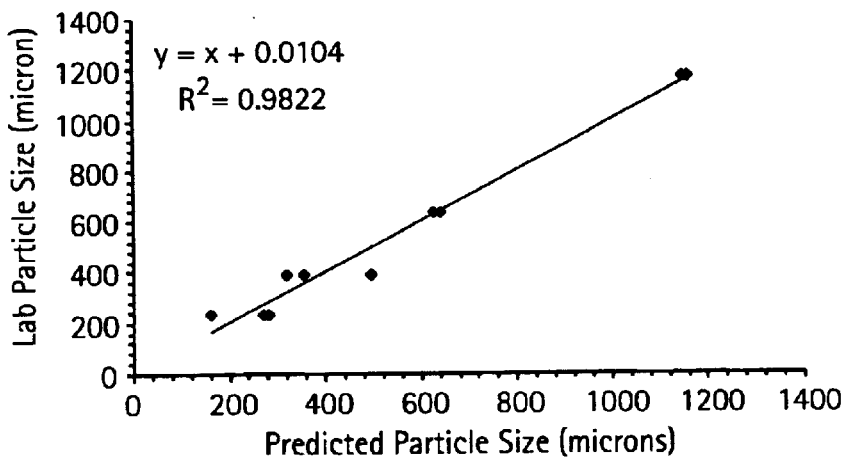
FIG. 2 is a graph showing the correlation between polyethylene particle size as predicted using a near-IR analyzed and the process of the present invention and as observed using conventional laboratory analyses.
Figure 3:
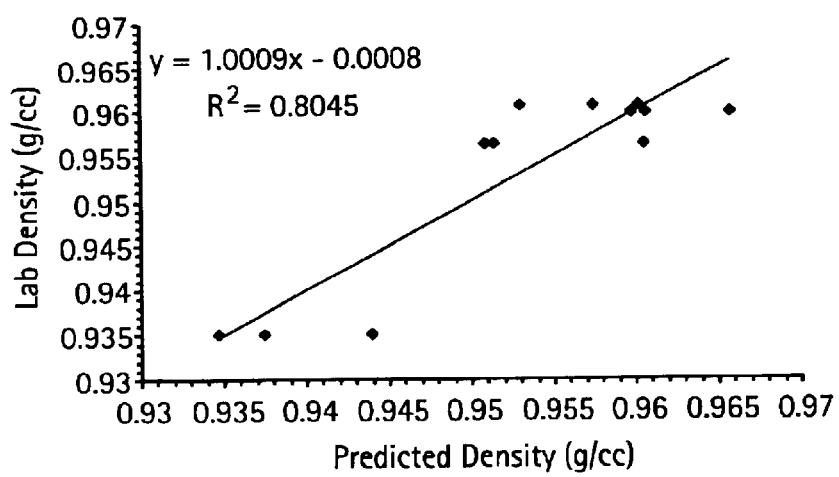
FIG. 3 is a graph showing the correlation between polyethylene density as predicted using a near-IR analyzed and the process of the present invention and as observed using conventional laboratory analyses.
Figure 4:
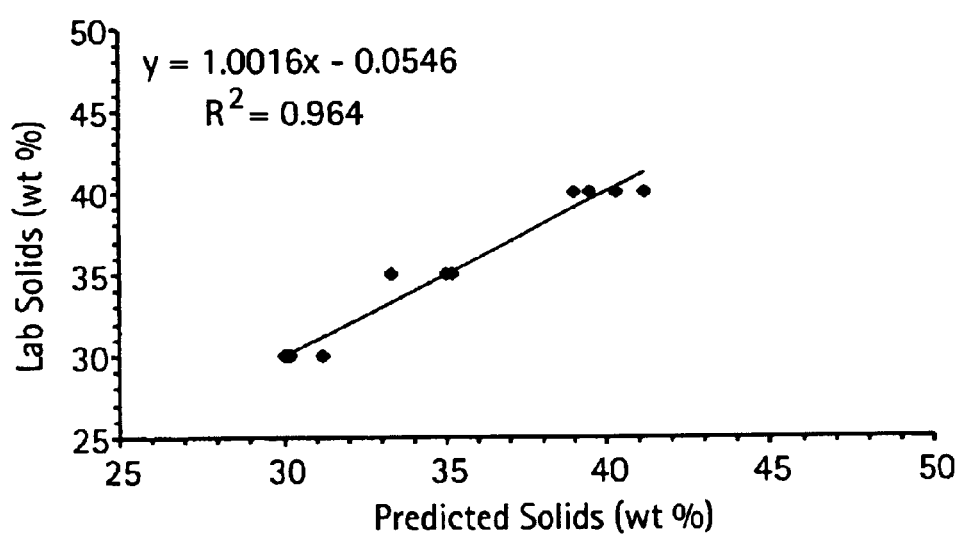
FIG. 4 is a graph showing the correlation between polyethylene solids weight percent as predicted using a near-IR analyzed and the process of the present invention and as observed using conventional laboratory analyses.

The values for these characteristics of interest and measured as in Example 1 and correlated against values determined using conventional laboratory practices. The resulting data is plotted and the graphs of those plots are attached as FIGS. 2–4.

Hypothetical Example 5

A polyethylene process is monitored as in Example 4. The values are inputted from the near-IR spectrophotometer to a laboratory information management software package being run on a PC. The PC displays a graph showing a downward drift in particle size. An operator in the unit notes the drift and, using a process control procedure, modifies the reactor temperature to bring the process back into specification.

Comments Regarding the Examples

Example 1 shows that the method of the present invention can be used to predict with good accuracy the values relating to the characteristics of interest for a process stream that can be used to control a impact modified polystyrene process. Example 4 does the same for a polyethylene process. The hypothetical Examples show the extent that a partially or even fully automated process control system can be used with the near-IR measurements to control a polymer process.

TABLE

| | 825E | | | 960E | | | 620 | | |
|---|---|---|---|---|---|---|---|---|---|
| Constituent | $R^2$ | Average % Error | Range | $R^2$ | Average % Error | Range | $R^2$ | Average % Error | Range |
| Styrene (wt fract) | 0.96 | 1.45 | 0.48–0.66 | 0.96 | 1.03 | 0.50–0.62 | 0.95 | 1.52 | 0.49–0.70 |
| Polystyrene (wt fract) | 0.98 | 2.05 | 0.20–0.35 | 0.97 | 3.06 | 0.13–0.33 | 0.97 | 2.08 | 0.16–0.32 |
| Diluents (wt fract) | 0.96 | 2.62 | 0.055–0.107 | 0.96 | 4.52 | 0.045–0.130 | 0.96 | 1.61 | 0.065–0.098 |
| RPS (micron) | 0.90 | 8.64 | 1.5–5.2 | 0.96 | 3.80 | 4.0–7.6 | 1.00 | 3.66 | 0.2–1.2 |
| Mineral Oil (wt fract) | 0.86 | 0.34 | 0.018–0.019 | 0.95 | 0.47 | 0.018–0.019 | 0.99 | 1.18 | 0.024–0.034 |
| Rubber (wt fract) | 0.96 | 0.21 | 0.062–0.066 | 0.96 | 0.43 | 0.95–0.105 | 0.98 | 0.15 | 0.076–0.078 |
| Temperature Range ° F. (° C) | 260–270 (127–132) | | | 230–240 (110–116) | | | 242–272 (117–133) | | |
| Samples (#) | 45 | | | 37 | | | 31 | | |

| | 975E | | | 7240 | | | Overall | | |
|---|---|---|---|---|---|---|---|---|---|
| Constituent | $R^2$ | Average % Error | Range | $R^2$ | Average % Error | Range | $R^2$ | Average % Error | Range |
| Styrene (wt fract) | 0.98 | 1.04 | 0.45–0.56 | 0.90 | 2.56 | 0.48–0.79 | 0.84 | 3.36 | 0.45–0.79 |
| Polystyrene (wt fract) | 0.96 | 2.40 | 0.27–0.35 | 0.93 | 3.78 | 0.10–0.30 | 0.96 | 4.62 | 0.10–0.35 |
| Diluents (wt fract) | 0.94 | 2.33 | 0.070–0.099 | 0.75 | 7.13 | 0.020–0.130 | 0.75 | 9.26 | 0.020–0.130 |
| RPS (micron) | 0.99 | 2.91 | 1.8–8.5 | 0.91 | 8.44 | 1.0–4.2 | 0.95 | 10.97 | 0.2–7.6 |
| Mineral Oil (wt fract) | 0.98 | 1.99 | 0.025–0.026 | 0.93 | 2.22 | 0.020–0.035 | 0.95 | 5.84 | 0.018–0.035 |
| Rubber (wt fract) | 0.93 | 0.24 | 0.077–0.079 | 0.89 | 1.08 | 0.070–0.082 | 0.94 | 2.82 | 0.062–0.105 |
| Temperature Range ° F. (° C) | 265–283 (129–139) | | | 230–280 (110–121) | | | 230–280 (110–121) | | |
| Samples (#) | 22 | | | 97 | | | 111 | | |

What is claimed is:

1. A process for preparing a polymer comprising preparing a polymer using a process having at least one process stream, the at least one process stream having at least one characteristic of interest, and the process further comprising passing the at least one process stream past a sensor probe connected to a near-IR spectrophotometer and passing light from a light source through the probe and into the spectrometer wherein the light source, spectrometer and sensor probe are connected by a fiber optic cable; and wherein the effect of the interaction of the process stream and the light passing through the senor probe is measured and used to define a value for the at least one characteristic of interest; and wherein the value for the at least one characteristic of interest is a component of an algorithm used in real time to monitor, control, or monitor and control the process for preparing a polymer.

2. The process of claim 1 wherein the polymer is polystyrene or polyethylene.

3. The process of claim 1 wherein the near-IR spectrophotometer scans a wavelength range of from about 750 to about 2500 microns nanometers.

4. The process of claim 3 wherein the near-IR spectrophotometer scans a wavelength range of from about 1100 to about 1800 nanometers.

5. The process of claim 1 wherein the near-IR spectrophotometer and the light source are separate.

6. The process of claim 1 wherein the near-IR spectrophotometer and the light source are an integrated unit.

7. The process of claim 1 wherein the probe is selected from the group consisting of transmittance probes, reflectance probes, and attenuated reflectance probes.

8. The process of claim 1 wherein the probe is in close proximity to the near-IR spectrophotometer.

9. The process of claim 1 wherein the probe is remote from the near-IR spectrophotometer.

10. The process of claim 1 additionally comprising interfacing the near-IR spectrophotometer to a process controller.

11. The process of claim 10 wherein the process controller is a, PID controller.

12. The process of claim 10 wherein the process controller is an artificial intelligence based controller.

13. The process of claim 12 wherein the artificial intelligence based controller is a neural net artificial intelligence controller.

14. The process of claim 1 wherein there are two probes connected to the near-IR spectrophotometer.

15. The process of claim 14 wherein both probes are in the same process stream.

16. The process of claim 14 wherein the probes are in separate process streams.

17. The process of claim 14 wherein the near-IR spectrophotometer is automated.

18. The process of claim 1 wherein the near-IR spectrophotometer incorporates a computer to perform some or all of the processes of interpreting spectra and making calculations therewith.

19. A process for preparing a polystyrene comprising preparing polystyrene using a process having at least one process stream, the at least one process stream having at least one characteristic of interest, and the process further comprising passing the at least one process stream past a sensor probe connected to a near-IR spectrophotometer and passing light from a light source through the probe and into the spectrometer wherein the light source, spectrometer and sensor probe are connected by a fiber optic cable; and wherein the effect of the interaction of the process stream and the light passing through the senor probe is measured and used to define a value for the at least one characteristic of interest; and wherein the value for the at least one characteristic of interest is a component of an algorithm used in real time to monitor, control, or monitor and control the process for preparing polystyrene.

20. The process of claim 19 wherein the characteristic of interest is selected from the group consisting of: styrene content, rubber particle size, polystyrene content, mineral oil, diluent, and rubber content.

21. A process for preparing a polyethylene comprising preparing polyethylene using a process having at least one process stream, the at least one process stream having at least one characteristic of interest, and the process further comprising passing the at least one process stream past a sensor probe connected to a near-IR spectrophotometer and passing light from a light source through the probe and into the spectrometer wherein the light source, spectrometer and sensor probe are connected by a fiber optic cable; and wherein the effect of the interaction of the process stream and the light passing through the senor probe is measured and used to define a value for the at least one characteristic of interest; and wherein the value for the at least one characteristic of interest is a component of an algorithm used in real time to monitor, control, or monitor and control the process for preparing polyethylene.

22. The process of claim 21 wherein the characteristic of interest is selected from the group consisting of: polyethylene solids content, polyethylene density, and polyethylene particle size.

* * * * *